(12) United States Patent
Mallard et al.

(10) Patent No.: US 10,925,814 B2
(45) Date of Patent: *Feb. 23, 2021

(54) CREAM GELS COMPRISING AT LEAST ONE RETINOID AND BENZOYL PEROXIDE

(71) Applicant: GALDERMA RESEARCH & DEVELOPMENT, Biot (FR)

(72) Inventors: Claire Mallard, Mougins (FR); Fabienne Louis, Villeneuve-Loubet (FR); Emmanuelle At Guillet, Antibes (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,190

(22) Filed: May 21, 2018

(65) Prior Publication Data
US 2018/0263865 A1    Sep. 20, 2018

Related U.S. Application Data

(60) Division of application No. 14/570,714, filed on Dec. 15, 2014, now Pat. No. 9,999,577, which is a continuation of application No. 12/457,788, filed on Jun. 22, 2009, now Pat. No. 8,957,112, which is a continuation of application No. PCT/FR2007/052613, filed on Dec. 21, 2007.

(30) Foreign Application Priority Data

Dec. 21, 2006 (FR) ..................... 06 55784

(51) Int. Cl.

| | | |
|---|---|---|
| *A61K 8/04* | (2006.01) |
| *A61K 8/38* | (2006.01) |
| *A61Q 19/00* | (2006.01) |
| *A61Q 19/08* | (2006.01) |
| *A61K 8/67* | (2006.01) |
| *A61K 9/06* | (2006.01) |
| *A61K 31/203* | (2006.01) |
| *A61K 31/327* | (2006.01) |
| *A61K 47/44* | (2017.01) |
| *A61K 8/11* | (2006.01) |
| *A61K 8/73* | (2006.01) |
| *A61K 8/81* | (2006.01) |
| *A61Q 5/00* | (2006.01) |
| *A61Q 7/00* | (2006.01) |
| *A61Q 17/04* | (2006.01) |

(52) U.S. Cl.
CPC ............ *A61K 8/04* (2013.01); *A61K 8/11* (2013.01); *A61K 8/38* (2013.01); *A61K 8/671* (2013.01); *A61K 8/73* (2013.01); *A61K 8/731* (2013.01); *A61K 8/8152* (2013.01); *A61K 8/8158* (2013.01); *A61K 9/06* (2013.01); *A61K 31/203* (2013.01); *A61K 31/327* (2013.01); *A61Q 5/00* (2013.01); *A61Q 5/008* (2013.01); *A61Q 7/00* (2013.01); *A61Q 17/04* (2013.01); *A61Q 19/00* (2013.01); *A61Q 19/008* (2013.01); *A61Q 19/08* (2013.01); *A61K 47/44* (2013.01); *A61K 2800/30* (2013.01); *A61K 2800/592* (2013.01); *A61K 2800/80* (2013.01); *A61K 2800/805* (2013.01)

(58) Field of Classification Search
CPC .......... A61K 8/04; A61K 9/06; A61K 31/203; A61K 8/671; A61K 8/38; A61K 31/327; A61P 17/08; A61Q 19/00; A61Q 19/008
See application file for complete search history.

(56) References Cited

U.S. PATENT DOCUMENTS

| | | |
|---|---|---|
| 3,535,422 A | 10/1970 | Cox et al. |
| 3,906,108 A | 9/1975 | Felty |
| 4,056,611 A | 11/1977 | Young |
| 4,189,501 A | 2/1980 | Fulton, Jr. |
| 4,355,028 A | 10/1982 | Kligman et al. |
| 4,717,720 A | 1/1988 | Shroot et al. |
| 4,725,429 A | 2/1988 | Scott et al. |
| 4,792,452 A | 12/1988 | Howard et al. |
| 4,960,772 A | 10/1990 | Sebag et al. |
| 5,035,890 A | 7/1991 | Braun |
| 5,204,093 A | 4/1993 | Victor |
| RE34,440 E | 11/1993 | Shroot et al. |
| 5,306,486 A | 4/1994 | McCook et al. |
| RE34,805 E | 12/1994 | Shroot et al. |
| 5,665,364 A | 9/1997 | McAtee et al. |
| 5,690,946 A | 11/1997 | Koulbanis et al. |

(Continued)

FOREIGN PATENT DOCUMENTS

| | | |
|---|---|---|
| CN | 1072843 A | 6/1993 |
| EP | 0 199 636 A1 | 10/1986 |

(Continued)

OTHER PUBLICATIONS

What is Acne? https://www.epiduoforte.com/about-acne, accessed May 26, 2020.*
International Search Report for corresponding PCT/FR2007/052613 dated Sep. 30, 2009, 7 pages.
Martin, et al., "Chemical stability of adapalene and tretinoin when combined with benzoyl peroxide in presence and in absence of visible light and ultraviolet radiation," British Journal of Dermatology, vol. 139, Suppl. 52, Oct. 1998, pp. 8-11.
"Community-based trial results of combination acne therapy in subjects with skin of color: Postinflammatory hyperpigmentation", Journal of the American Academy of Dermatology, C.V. Mosby, St. Louis, MO, vol. 58, No. 2, Feb. 1, 2008, p. AB13, XP022456844, ISSN: 0190-9622.

(Continued)

*Primary Examiner* — H. Sarah Park
(74) *Attorney, Agent, or Firm* — Foley & Lardner LLP; Sunil Talapatra

(57) ABSTRACT

Stable cream gel dermatological/cosmetic compositions useful, e.g., for the treatment of acne vulgaris, contain, formulated into a physiologically acceptable medium, a homogeneous dispersion of at least one dispersed retinoid, dispersed benzoyl peroxide, at least one lipophilic compound and at least one gelling agent.

8 Claims, No Drawings

(56) References Cited

U.S. PATENT DOCUMENTS

| | | | |
|---|---|---|---|
| 5,707,635 A | 1/1998 | Deckner et al. | |
| 5,733,886 A | 3/1998 | Baroody et al. | |
| 5,824,650 A | 10/1998 | De Lacharriere et al. | |
| 6,010,706 A | 1/2000 | Candau et al. | |
| 6,106,848 A | 8/2000 | Preuilh et al. | |
| 6,274,151 B1 | 8/2001 | Michel et al. | |
| 6,413,536 B1 | 7/2002 | Gibson et al. | |
| 6,423,324 B1 | 7/2002 | Murphy et al. | |
| 6,559,189 B2 | 5/2003 | Baker et al. | |
| 7,060,732 B2 | 6/2006 | Vishnupad et al. | |
| 7,368,122 B1 | 5/2008 | Dow et al. | |
| 7,700,076 B2 | 4/2010 | Tamarkin et al. | |
| 7,820,186 B2 | 10/2010 | Orsoni et al. | |
| 7,964,202 B2 | 6/2011 | Orsoni et al. | |
| 8,105,618 B2 | 1/2012 | Orsoni-Segona et al. | |
| 8,241,649 B2 | 8/2012 | Orsoni et al. | |
| 8,445,543 B2 | 5/2013 | Abou-Chacra Vernet et al. | |
| 8,568,704 B2 | 10/2013 | Mallard et al. | |
| 8,785,420 B2 | 7/2014 | Abou Chacra Vernet et al. | |
| 8,937,098 B2 | 1/2015 | Mallard et al. | |
| 2002/0035161 A1 | 3/2002 | Segura et al. | |
| 2002/0039561 A1 | 4/2002 | Doughty et al. | |
| 2002/0064541 A1 | 5/2002 | Lapidot et al. | |
| 2002/0165286 A1 | 11/2002 | Hedeman et al. | |
| 2003/0021855 A1 | 1/2003 | Perricone | |
| 2003/0157138 A1 | 8/2003 | Eini et al. | |
| 2003/0170196 A1* | 9/2003 | Orsoni | A61K 31/07 424/70.17 |
| 2004/0157766 A1 | 8/2004 | Embil et al. | |
| 2004/0167223 A1 | 8/2004 | Popp | |
| 2005/0074414 A1 | 4/2005 | Tamarkin et al. | |
| 2005/0148495 A1 | 7/2005 | Lambert et al. | |
| 2005/0163731 A1 | 7/2005 | Pelisson et al. | |
| 2005/0181999 A1 | 8/2005 | Ferrandis et al. | |
| 2005/0238612 A1* | 10/2005 | Courcoux | A61K 8/97 424/74 |
| 2005/0239043 A1 | 10/2005 | Harding | |
| 2005/0239723 A1 | 10/2005 | Amin et al. | |
| 2006/0128808 A1 | 6/2006 | Arsonnaud et al. | |
| 2006/0233735 A1 | 10/2006 | Preuilh et al. | |
| 2006/0234981 A1 | 10/2006 | Baker et al. | |
| 2007/0003585 A1 | 1/2007 | Clark et al. | |
| 2007/0044810 A1 | 3/2007 | Ramirez et al. | |
| 2007/0237724 A1 | 10/2007 | Abram et al. | |
| 2008/0181963 A1 | 7/2008 | Orsoni et al. | |
| 2009/0191245 A1 | 7/2009 | Fredon et al. | |
| 2009/0226380 A1 | 9/2009 | Clark et al. | |
| 2009/0298798 A1 | 12/2009 | Abou-Chacra Vernet et al. | |
| 2010/0143445 A1 | 6/2010 | Pelisson et al. | |
| 2012/0115947 A1 | 5/2012 | Chacra Vernet et al. | |

FOREIGN PATENT DOCUMENTS

| | | |
|---|---|---|
| EP | 0 335 115 A2 | 2/1989 |
| FR | 2618673 | 7/1968 |
| FR | 2225167 A1 | 11/1974 |
| FR | 2378523 | 1/1977 |
| FR | 2628319 | 3/1988 |
| FR | 2687312 A1 | 8/1993 |
| FR | 2718018 A1 | 10/1995 |
| FR | 2730930 A1 | 8/1996 |
| FR | 2753626 A1 | 9/1996 |
| FR | 2833841 A1 | 6/2003 |
| FR | 2909000 A1 | 5/2008 |
| FR | 2910321 A1 | 6/2008 |
| GB | 1 594 314 | 1/1978 |
| GB | 2 088 717 A | 6/1982 |
| GB | 2 130 486 A | 6/1984 |
| GB | 2 207 353 | 7/1987 |
| HU | 218936 | 12/1995 |
| HU | 218592 | 6/1996 |
| JP | H01100134 | 4/1989 |
| JP | H01268632 | 10/1989 |
| JP | H07500593 | 1/1995 |
| WO | 81/00206 A1 | 2/1981 |
| WO | WO-93/07856 | 4/1993 |
| WO | 93/20796 A1 | 10/1993 |
| WO | WO-95/31978 | 11/1995 |
| WO | WO-99/65456 A1 | 6/1999 |
| WO | 99/44586 A1 | 9/1999 |
| WO | WO-99/044596 | 9/1999 |
| WO | WO-9944586 A1 * | 9/1999 ............... A61K 8/06 |
| WO | WO-00/37027 | 12/1999 |
| WO | WO-01/45647 | 6/2001 |
| WO | 03/055472 A1 | 7/2003 |
| WO | WO-03/075908 A1 | 9/2003 |
| WO | WO-2004/064833 A1 | 8/2004 |
| WO | 2006/099192 A2 | 9/2006 |
| WO | WO-2007/002831 A | 1/2007 |
| WO | WO-2007/007198 | 1/2007 |
| WO | WO-2007/092312 A2 | 8/2007 |
| WO | WO-2008/006888 A1 | 1/2008 |
| WO | WO-2008/007224 A2 | 1/2008 |
| WO | WO-2008/008397 | 1/2008 |
| WO | WO-2008/087354 | 7/2008 |
| WO | WO-2009/068610 | 6/2009 |
| WO | WO-2009/069006 A2 | 6/2009 |
| WO | WO-2009/130326 A1 | 10/2009 |
| WO | WO-2011/038446 A1 | 4/2011 |
| WO | WO-2011/098391 | 8/2011 |
| WO | WO-2011/135090 | 11/2011 |
| WO | WO-2015/091828 | 6/2015 |

OTHER PUBLICATIONS

"Wetting agents" (http://www.innovateus.net/print/science/what-are-wetting-agents) accessed Jan. 23, 2015 (Year: 2015).

Alirezai et al: "Etude Comparative De L'Efficacite et de La Tolerance de Gels D'Adapalene A O, 1 et 0,03, P.100 et D'un Gel de Tretinoine A 0, 025 P.100 Dans le Traitement de L'acne" Annales de Dermatologie et de Venereologie, Paris, FR, vol. 123, No. 3, 1996, pp. 165-170, XP000974556, ISSN: 0151-9638.

Ashland Inc. Ashland Carbomer, Published before 2001, pp. 1-8.

Bershard, S.V., "The modem age of acne therapy: a review of current treatment options," Mt Sinai J Med Sep.-Oct. 2001; 68(4-5); 279-86.

Bikowski, "Clinical Experience Results with Clindamycin 1% Benzoyl Peroxide 5% Gel (Duac®) as Monotherapy and in Combination", Journal of Drugs in Dermatology, Mar. 2005, pp. 164-171, vol. 4, No. 2.

Brand et al., "Cumulative irritancy comparison of adapalene gel 0.1 % versus other retinoid products when applied in combination with topical antimicrobial agents", J. Am. Acad. Dermatol., Sep. 2003, pp. S227-S232, vol. 49, No. 3, Cranbury, NJ.

Callender, V D et al., "A meta-analysis to investigate the relation between Fitzpatrick skin types and tolerability of adapalene-benzoyl peroxide topical gel in subjects with mild or moderate acne," Journal of Clinical and Aesthetic Dermatology, 2010, Matrix Medical Communications, USA, vol. 3, No. 8, Jul. 2010, pp. 15-19.

Capizzi et al., "Skin tolerability and efficacy of combination therapy with hydrogen peroxide stabilized cream and adapalene gel in comparison with benzoyl peroxide cream and adapalene gel in common acne. A randomized, investigator-masked, controlled trial", British Journal of Dermatology, 2004, pp. 481-484, vol. 151, No. 2.

Capizzi, et al., "Efficacy and Safety of Combination Therapy of Hydrogen Peroxide Cream and Adapalene Gel in Comparison with Benzoyl Peroxide Cream and Adapalene in Common Acne," Journal of the American Academy of Dermatology, vol. 50, Issue 3, Supplement 1, p. P18 (Mar. 2004 ).

Caron et al. "Skin Tolerance of Adapalene 0.1% Gel in Combinatoin with other Topical Antiacne Treatments," Journal of the American Academy of Dermatology. vol. 36, No. 6, Part 2. 1997 ppgs. S113-S115.

Cassano N, et al., "Treatment of mild to moderate acne vulgaris with adapalene alone or combined with other anti-acne agents. A multicenter open trial", Giornale Italiano Di Dermatologia E Venereologia,(2002), vol. 137, No. 5, pp. 369-375.

(56) References Cited

OTHER PUBLICATIONS

Cassano,N., et al., "Treatment of inflammatory acne with a combination therapy with lymecycline and adapalene followed by maintenance treatment with adapalene", European Journal of Inflammation, (2004), Italy, vol. 2, No. 1, pp. 45-52.
Chellquist et al., "Benzoyl Peroxide Solubility and Stability in Hydric Solvents," Pharmaceutical Research, vol. 9, No. 10, 1992, . 1341-1346, ublished b S rin er, The Netherlands.
Clucas et al., "Adapalene 0.1 % gel has low skin irritation potential", Journal of the European Academy of Dermatology and Venereology, Sep. 1998, p. S275, vol. 11, Elsevier Science Publisher.
Coley, M K et al., "Managing Common Dermatoses in Skin of Color," Seminars in Cutaneous Medicine and Surgery, W.B. Saunders, Philadelphia, US, vol. 28, No. 2, Jun. 1, 2009, pp. 63-70, XP026301340, ISSN: 1085-5629, DOI: 10.1016/J.SDER.2009.04.006.
Czernielewski et al., "Adapalene biochemistry and the evolution of a new topical retinoid for treatment of acne", Journal of European Academy of Dermatology and Venerology. Dec. 2001, vol. 15, Supplement 3, pp. 5-12.
Czernielewski et al., "Efficacy and Cutaneous Safety of Adapalene in Black Patients Versus White Patients with Acne Vulgaris", Therapeutics for the Clinician, vol., 70, Oct. 2002, p. 243-248.
Differin Gel Data Sheet, available as of Nov. 1998, pp. 1-5.
Do Nascimento L V Et al: "Single-Blind and Comparative Clinical Study of the Efficacy and Safety of Benzoyl Peroxide 4% Gel (BID) and Adapalene 0.1% Gel (QD) in the Treatment of Acne Vulgaris for 11 Weeks," Journal of Dermatological Treatment, Basingstoke, GB, vol. 14, No. 3, Jan. 1, 2003, pp. 166-171, XP008073256, ISSN: 0954-6634.
Draelos, Z. Dermatologic Therapy, vol. 20, 2007, p. 308-313.
Elmore, "Final report on the safety assessment of aluminum silicate, calcium silicate, magnesium aluminum silicate, magnesium silicate, magnesium trisilicate, sodium magnesium silicate, zirconium silicate, attapulgite, bentonite, Fuller's earth, hectorite, kaolin, lithium magnesium silicate, lithium magnesium sodium silicate, montmorillonite, pyrophyllite, and zeolite." 2003, International Journal of Toxicology, 22 (Suppl. 1), pp. 37-102.
FDA label for Differin 0.1 % gel, NOA No. 020380 (3 pages).
Fitzpatrick et al., "The Validity and Practicality of sun-reactive skin types I through VI", Archives of Dermatology, vol. 124, No. 6, 1988, pp. 869-871.
Gollnick et al., "Adapalene-benzoyl peroxide, a unique fixed-dose combination topical gel for the treatment of acne vulgaris: a transatlantic, randomized, double-blind, controlled study in 1670 patients", British Journal of Dermatology, 2009, 161, pp. 1180-1189.
Gollnick et al., "Evaluation of a maintenance treatment acne vulgaris with adapalene gel, 0.1%" JEADV (2004) 18 (Suppl. 2), 193-557).
Hurwitz. "The Combined Effect of Vitamin A Acid and Benzyl Peroxide in the Treatmetn of Acne". vol. 17 No. 3, Mar. 1976. pp. 585-590.
Jamoulle et al., "Follicular penetration and distribution of topically applied CD 271, a new napthoic acid derivative intended for topical acne treatment" Journal of Investigative Dermatology (1990), 94(5), 731-2, XP008010277.
Josaine et al: "Skin distribution and pharmaceutical aspects of adapalene gel." Journal of the American Academy of Dermatology,vol. 36, No. 6, part 2, 1997, pp. S119-S125, XP008010230, ISSN: 0190-09622.
Kang Sewon, et al., "Assessment of adapalene gel for the treatment of actinic keratoses and lentigines: a randomized trial", Journal of the American Academy of Dermatology, (2003), vol. 49, No. 1, pp. 83-90. DOI: http://dx.doi.org/10.1067/mid.2003.451.
Kimball, A. B. "Skin Differences, Needs, and Disorders across Global Populations," Journal of Investigative Dermatology Symposium Proceedings (2008) 13, 2-5.
Korkut et al., "Benzoyl Peroxide, Adapalene, and their Combination in the Treatment of Acne Vulgaris", The Journal of Dermatology, 2005, pp. 169-173, vol. 32, No. 3, Edirne, Turkey.

Leyden, et al., "Photographic Review of Results From a Clinical Study Comparing Benzoyl Peroxide 5%/Clindamycin 1 % Topical Gel with Vehicle in the Treatment of Rosacea," Topical Treatment for the Inflamed Lesion in Acne, Rosacea, and Pseudofolliculitis Barbae, Jun. 2004, vol. 73, p. 3.
Leyden, James J., "A Review of the Use of Combination Therapies for the Treatment of Acne Vulgaris," Journal of the American Academy of Dermatology, vol. 49, No. 3, pp. S200-S210 (Sep. 2003).
Menlo Dermatology Medical Group and Laser Center, Inc. http://www.mdmg.com/general-dermatology/general-1/ (2019).
Michalun et al., "Milady's Skin Care and Cosmetic Ingredients Dictionary," Milady Publishing Company, Albany, NY, p. 175.
Millikan, "Adapalene: an update on newer comparative studies between the various retinoids," International Journal of Dermatology, vol. 39, Issue 10, Oct. 2000, pp. 784-788.
Mills Jr. et al., "Comparing 2.5%, 5% and 10% benzoyl peroxide on inflammatory acne vulgaris" In. J. Dermatology. 1986, pp. 664-667.
Piskin, S. et al. "A review of the use of adapalene for the treatment fo acne vulgaris," Therapeutics and Clinical risk Management, 2007, 3(4), pp. 621-624 (Year: 2007).
Pongjanyakul et al., "Influence of magnesium aluminium silicate on rheological, release and permeation characteristics of diclofenac sodium aqueous gels in-vitro," Journal of Pharmacy and Pharmacology, vol. 57, Issue 4, Apr. 2005, pp. 429-434, abstract.
Rel Yveld et al., "Benzoyl peroxide/clindamycin/UVA is more effective than fluticasone/UVA in progressive macular hypomelanosis: A randomized study," J. Am. Acad. Dermatol., Nov. 2006, vol. 55, No. 5, pp. 836-843.
Rolland et al: "Site-specific drug delivery to pilosebaceous structures using polymeric microspheres." Pharmaceutical Research. United States Dec. 1993, vol. 10, No. 12, Dec. 1993 (1993-12), pp. 1738-1744, XP008010243, ISSN: 0724-8741.
Sepicontrol A5, "Purifying dermoprotector: For the treatment of oily, acne prone skins", Aug. 2001, pp. 1-53.
Sepigel (http://www.farmalabor.it/schede/2014/119590.PDF) accessed Dec. 7, 2016, pp. 1-2. (Year: 2016).
SEPPIC Personal Care Ingredients Catalog, pp. 1-26 and endnotes, 2004/rev. 2006, published by SEPPIC S.A., L on, France.
Shroot et al: "A new concept of drug delivery for acne." Dermatology (Basel),vol. 196, No. 1, 1998, pp. 165-170, XP008010229, ISSN: 1018-8665.
Talukdar et al., "Rheological Characterization of Xanthan Gum and Hydroxypropylmethyl Cellulose with Respect to Controlled-Release Drug Delivery", Journal of Pharmaceutical Sciences, May 1996, vol. 85, No. 5, pp. 537-540.
Taylor., "Utilizing Combination Therapy for Ethnic Skin", Cutis, Excerpta Medica, Belle Mead, NJ, US, vol. 80, No. 1, Jul. 1, 2007, pp. 15-20, XP009120299, ISSN: 0011-4162.
Van Zuuren, et al., "Systematic review of rosacea treatments," J. Am. Acad. Dermatol., Jan. 2007, vol. 56, No. 1, pp. 107-115.
Walker, Susan J., M.D., "Summary Review" dated Dec. 1, 2008, NDA No. 22-320 (6 pages).
Weiss et al., "Adapalene for the treatment of acne vulgaris", Journal of the American Academy of Dermatology, Aug. 1998, pp. S50-S54, vol. 39, No. 2.
Wen-Wen et al., "Clinical efficacy and safety of 5% benzoyl peroxide gel combined with 0.1 % adapalene gel in the treatment of acne vulgaris: a multicenter randomized study", Database Biosis, Biosciences Information Service, Jun. 2003, Database accession No. PREV200300514701, pp. 310-312, vol. 36, No. 6.
Zhang et al., "A successful maintenance approach in inflammatory acne with adapalene gel 0.1% after an initial treatment in combination with clindamycin topical solution 1% or after monotherapy with clindamycin topical solution 1%", The Journal of Dermatological Treatment, (2004), vol. 15, No. 6, pp. 372-378. DOI: http://dx.doi.org/10.1080/09546630410021702.
Gollnick et al., "Evaluation of a maintenance treatment acne vulgaris with adapalene gel, 0.1%" JEADV (2004) 18 (Suppl. 2), pp. 193-557.
Healy et al., "Acnevulgaris", British Medical Journal, 1994, vol. 308, Iss. 6932, pp. 2-9.

(56) References Cited

OTHER PUBLICATIONS

Hercules, "Product Data: Natrosol(r) 250 water soluble hydroxyethylcellulose," 2005, Aqualon, accessed online Nov. 1, 2010 [http://www.in-cosmetics.com/ExhibitorLibrary/108/33015e11.pdf].

Thiboutot et al., "Adapalene-benzoyl peroxide, a fixed-dose combination for the treatment of acne vulgaris: results of a multicenter, randomized double-blind, controlled study", J Am Acad Dermatol, vol. 57, No. 5, Nov. 2007 (9 pages).

\* cited by examiner

CREAM GELS COMPRISING AT LEAST ONE RETINOID AND BENZOYL PEROXIDE

CROSS-REFERENCE TO PRIOR APPLICATIONS

This application is a divisional of U.S. application Ser. No. 14/570,714, filed Dec. 15, 2014, with is a continuation of U.S. application Ser. No. 12/457,788, filed Jun. 22, 2009, now U.S. Pat. No. 8,957,112, which is a continuation of PCT/FR2007/052613, filed Dec. 21, 2007 and designating the United States (published in the French language on Jul. 24, 2008 as WO 2008/087354 A2; the title and abstract were also published in English), which claims priority under 35 U.S.C. § 119 of French Patent Application No. FR 0655784, filed Dec. 21, 2006, each hereby expressly incorporated by reference in its entirety and each assigned to the assignee hereof.

BACKGROUND OF THE INVENTION

Technical Field of the Invention

The present invention relates to dermatological compositions in the form of a cream gel comprising, formulated into a physiologically acceptable medium, at least one dispersed retinoid and dispersed benzoyl peroxide.

Description of Background and/or Related and/or Prior Art

The use of several categories of active principles is a therapeutic tool to which recourse is frequently had, in particular in the treatment of dermatological disorders.

Specifically, different anti-fungals, such as allylamine derivatives, triazoles, antibacterials or anti-microbials, such as, for example, antibiotics, quinolones and imidazoles are conventionally combined in the treatment of dermatological diseases/afflictions. It is also known to administer peroxides, vitamins D and retinoids in the topical treatment of various pathologies related to the skin or mucous membranes, in particular acne.

The combination of several local treatments (antibiotics, retinoids, peroxides, zinc) is also employed in dermatology to make it possible to enhance the effectiveness of the active principles and to reduce their toxicity (Cunliffe W. J., *J. Dermatol. Treat.*, 2000, 11 (suppl.2), S13-S14).

The multiple application of different dermatological products may be fairly burdensome and demanding for the patient.

The interest in attempting to obtain a novel treatment which is effective with regard to dermatological conditions in a stable composition which offers a good cosmetic quality, which makes possible a single application and which makes possible a use which is agreeable to the patient is thus understood.

Nothing exists among this range of therapies that would encourage one skilled in the art to combine, in the same composition, benzoyl peroxide and a retinoid.

However, the formulation of such a composition presents several problems.

First of all, the effectiveness of the benzoyl peroxide is related to its decomposition when it is brought into contact with the skin. This is because it is the oxidizing properties of the free radicals produced during this decomposition which result in the desired effect. Consequently, in order for the benzoyl peroxide to maintain an optimum effectiveness, it is important to prevent it from decomposing before use, that is to say during storage.

In point of fact, benzoyl peroxide is an unstable chemical compound, which makes it difficult to formulate it in finished products.

The solubility and the stability of benzoyl peroxide have been studied by Chellquist et al., in ethanol, propylene glycol and various mixtures of polyethylene glycol 400 (PEG 400) and water (Chellquist E. M. and Gorman W. G., *Pharm Res.*, 1992, Vol. 9, 1341-1346).

Benzoyl peroxide is particularly soluble in PEG 400 and ethanol, as is shown in the following table:

| Solvent | Solubility of benzoyl peroxide (mg/g) |
| --- | --- |
| PEG 400 | 39.6 |
| Ethanol | 17.9 |
| Propylene glycol | 2.95 |
| Propylene glycol/water (75:25) | 0.36 |
| Glycerol | 0.15 |
| Water | 0.000155 |

This document furthermore specifies that the stability of benzoyl peroxide is strongly influenced by the chemical composition of the formulation and by the storage temperature. Benzoyl peroxide is highly reactive and decomposes in solution at low temperature due to the instability of its peroxide bond.

The authors thus find that benzoyl peroxide in solution decomposes more or less rapidly in all the solvents studied according to the type of solvent and its concentration.

The decomposition times of benzoyl peroxide in PEG 400 (0.5 mg/g), in ethanol and in propylene glycol are 1.4, 29 and 53 days respectively at 40° C.

Such a decomposition does not make possible the formulation of a product useful for sale.

Furthermore, it is known that benzoyl peroxide is more stable in water and propylene glycol when it is in suspension (i.e., in the dispersed form), since it is not decomposed after storing for 90 days in these solvents.

Thus, to limit the problem of rapid instability of benzoyl peroxide in solution, it has proven to be advantageous to formulate benzoyl peroxide in the dispersed form. However, this type of formulation is not completely satisfactory insofar as the benzoyl peroxide is still found to be decomposed in the finished product.

Another difficulty to be overcome in the preparation of a composition comprising both benzoyl peroxide and a retinoid is that the majority of retinoids are particularly sensitive to natural oxidation, to visible light and ultraviolet radiation and, as benzoyl peroxide is a strong oxidizing agent, the chemical compatibility of these compounds in one and the same formulation presents numerous problems of stability from the physical and chemical viewpoint.

A stability study was carried out on two retinoids by combining two commercial products, one comprising a retinoid (tretinoin or adapalene) and the second based on benzoyl peroxide (B. Martin et al., *Br. J. Dermatol.*, (1998) 139, (suppl. 52), 8-11).

The presence of the formulation based on benzoyl peroxide causes very rapid decomposition of the oxidation-sensitive retinoids: 50% of the tretinoin is measured as decomposing in 2 hours and 95% in 4 hours. In the composition in which the retinoid is adapalene, no decomposition of the adapalene was measured during 24 hours. This study confirms that benzoyl peroxide is decomposed and decomposes oxidation-sensitive retinoids over time by gradually releasing benzoic acid in finished products.

In point of fact, it is clear that the decomposition of benzoyl peroxide and retinoids is not desirable insofar as it is harmful to the effectiveness of the composition in which they are present.

Nothing would suggest combining of these two active agents to obtain a stable composition of emulsion type, it being known that it was conventionally recognized that the presence of benzoyl peroxide chemically and physically destabilized this type of composition.

The formulation as a cream gel of benzoyl peroxide and a retinoid can be advantageous for topical treatments, such as that of acne, as, while contributing emollience, it avoids in particular leaving an excessively greasy feel remaining on the skin.

In point of fact, another difficulty to be overcome in the preparation of such a composition comprising in particular dispersed active principles, such as adapalene and benzoyl peroxide, is the sedimentation of the active principles. This is because, while the "light" feel of such a formulation is related to the fact that the external phase is aqueous, it also depends on its composition and in particular on the presence of thickeners. In point of fact, in cream gels, the thickeners for the fatty phase, such as waxes and solid fatty alcohols and esters, are greatly reduced, to the advantage of gelling agents for the aqueous phase. However, the majority of gelling agents for the aqueous phase are destabilized by the benzoic acid which is released during the decomposition of the benzoyl peroxide.

Specifically, the thickening agents most commonly used for the formulation of gels with benzoyl peroxide are acrylic acid polymers (Carbomer) and celluloses, alone or in combination with silicates.

In point of fact, the use of carbomers in compositions of aqueous gel type does not give good results in terms of chemical stability of the benzoyl peroxide and in terms of rheological stability. As described by Bollinger (Bollinger, Journal of Pharmaceutical Science, 1977, Vol. 5), a loss of 5% to 20% of benzoyl peroxide after 2 months at 40° C., depending on the neutralizing agent of the carbomer used, was observed. Furthermore, the release of benzoic acid brings about depolymerization of the carbomers, giving a fall in viscosity which may bring about phase separation.

In other gels composed of a mixture of hydroxypropylcellulose and of magnesium aluminum silicate, a drop in viscosity over time is also observed and results in sedimentation of the suspended active principles and in the dispersion in the finished product being heterogeneous.

This instability of benzoyl peroxide gels is harmful to their effectiveness and to their cosmetic quality and it is highly probable that it is reencountered in cream gels. A finished product, in particular when it concerns pharmaceutical or cosmetic compositions, must maintain, throughout its lifetime, precise physicochemical criteria which make it possible to guarantee its pharmaceutical or cosmetic quality respectively. Among these criteria, it is necessary for the rheological properties to be retained. They define the behavior and the texture of the composition during application but also the properties of release of the active principle [SFSTP Commission report 1998] and the homogeneity of the product when the active principles are present therein in the dispersed state.

The need thus exists to have available a physically and chemically stable cream gel comprising benzoyl peroxide and a retinoid.

SUMMARY OF THE INVENTION

Dermatological compositions have now been developed which meet this need. Such compositions are cream gels which comprise:

dispersed benzoyl peroxide, in particular in the free or encapsulated form, at least one retinoid, at least one lipophilic compound constituting the fatty phase, and at least one pH-independent gelling agent which has good physical stability, that is to say which does not exhibit a drop in viscosity over time and at temperatures of from 4° C. to 40° C., and which maintains good chemical stability for the two active principles (benzoyl peroxide and retinoid), that is to say that decomposition of active principles over time and at temperatures from 4° C. to 40° C. is not observed.

The compositions of the present invention can be provided in all the formulation forms normally employed for topical application and in particular in the form of a cream gel with a semiliquid consistency of the milk type or with a solid consistency of the cream type obtained by dispersion of a fatty phase in an aqueous phase (O/W).

One skilled in this art will take care to select the excipients constituting the compositions according to the invention as a function of the consistency desired and so that the advantageous properties of the composition are maintained.

DETAILED DESCRIPTION OF BEST MODE AND SPECIFIC/PREFERRED EMBODIMENTS OF THE INVENTION

The compositions according to the invention can in particular comprise, in addition to at least one retinoid, benzoyl peroxide, a fatty phase and at least one pH-independent gelling agent, one or more of the following ingredients:

a) one or more wetting agents,
b) one or more chelating agents,
c) an aqueous phase,
d) one or more additives.

It has now surprisingly been determined that it is possible to obtain a perfect dispersion of active principles by following a specific preparation process. This preparation process makes it possible to obtain an optimum particle size and a homogeneous dispersion of the two active principles in the composition while guaranteeing the physical stability of the product.

The present invention thus features dermatological compositions in the form of cream gels comprising, formulated into a physiologically acceptable medium, at least one dispersed retinoid and dispersed benzoyl peroxide.

The compositions according to the invention are preferably in the form of an aqueous cream gel.

The cream gel is characterized by the presence of gelling agents for the aqueous phase and of a fatty phase. On the other hand, there is (are) no emulsifier(s) which differentiates cream gels from emulsions.

The term "emulsifiers" means amphiphilic compounds which have a hydrophobic part having an affinity for the oil and a hydrophilic part having an affinity for the water, thus creating a connection from the two phases. Ionic or nonionic emulsifiers thus stabilize O/W emulsions by being adsorbed at the interface and by forming lamellar layers of liquid crystals.

In particular, the compositions according to the invention are physically and chemically stable.

The term "physiologically acceptable medium" means a medium compatible with topical application on the skin, superficial body growths and/or mucous membranes.

The compositions according to the invention comprise at least one retinoid. The term "retinoid" means any compound which binds to RAR and/or RXR receptors.

Exemplary are, as retinoid, retinoic acid, tretinoin, tazarotene and those described in the following:
U.S. Pat. Nos. 4,666,941, 4,581,380, EP 0210929, EP 0232199, EP 0260162, EP 0292348, EP 0325540, EP 0359621, EP 0409728, EP 0409740, EP 0552282, EP 0584191, EP 0514264, EP 0514269, EP 0661260, EP 0661258, EP 0658553, EP 0679628, EP 0679631, EP 0679630, EP 0708100, EP 0709382, EP 0722928, EP 0728739, EP 0732328, EP 0749937, EP 0776885, EP 0776881, EP 0823903, EP 0832057, EP 0832081, EP 0816352, EP 0826657, EP 0874626, EP 0934295, EP 0915823, EP 0882033, EP 0850909, EP 0879814, EP 0952974, EP 0905118, EP 0947496, WO98/56783, WO99/10322, WO99/50239 and WO99/65872.

Due to their ability to bind RAR and/or RXR receptors, the compounds resulting from the family of the benzonaphthalene retinoids, such as described in EP 0199636, are also included in the invention.

Preferably, the naphthoic acid derivatives will be selected and in particular:
6-(3-methylphenyl)-2-naphthoic acid and its methyl ester,
6-(4-(tert-butyl)phenyl)-2-naphthoic acid and its methyl ester,
6-(3-(tert-butyl)phenyl)-2-naphthoic acid and its methyl ester,
6-(3,4-dimethoxyphenyl)-2-naphthoic acid and its methyl ester,
6-(p-(1-adamantylthio)phenyl)-2-naphthoic acid and its methyl ester,
6-(3-(1-adamantyl)-4-methoxyphenyl)-2-naphthoic acid (adapalene) and its methyl ester,
the methyl ester of 6-[3-(1-adamantyl)-4-(tert-butyldimethylsilyloxy)phenyl]-2-naphthoic acid,
the methyl ester of 6-[3-(1-adamantyl)-4-hydroxyphenyl]-2-naphthoic acid,
6-[3-(1-adamantyl)-4-hydroxyphenyl]-2-naphthoic acid,
the methyl ester of 6-[3-(1-adamantyl)-4-decyloxyphenyl]-2-naphthoic acid,
6-[3-(1-adamantyl)-4-decyloxyphenyl]-2-naphthoic acid,
the methyl ester of 6-[3-(1-adamantyl)-4-hexyloxyphenyl]-2-naphthoic acid,
6-[3-(1-adamantyl)-4-hexyloxyphenyl]-2-naphthoic acid,
the methyl ester of 6-[3-(1-adamantyl)-4-methoxyphenyl]-4-acetoxy-1-methyl-2-naphthoic acid,
6-[3-(1-adamantyl)-4-methoxyphenyl]-4-hydroxy-1-methyl-2-naphthoic acid,
the methyl ester of 6-[3-(1-adamantyl)-4-methoxyphenyl]-4-hydroxy-1-methyl-2-naphthoic acid,
the methyl ester of 6-[3-(1-adamantyl)-4-methoxyphenyl]-1-methyl-2-naphthoic acid,
6-[3-(1-adamantyl)-4-methoxyphenyl]-1-methyl-2-naphthoic acid,
6-[3-(1-adamantyl)-4-methoxyphenyl]-2-naphthalenemethanol,
the ethyl amide of 6-[3-(1-adamantyl)-4-methoxyphenyl]-2-naphthoic acid,
the morpholide of 6-[3-(1-adamantyl)-4-methoxyphenyl]-2-naphthoic acid,
the methyl ester of 6-[3-(tert-butyl)-4-methoxyphenyl]-2-naphthoic acid,
6-[3-(tert-butyl)-4-methoxyphenyl]-2-naphthoic acid,
the methyl ester of 6-[3-(1,1-dimethyldecyl)-4-methoxyphenyl]-2-naphthoic acid,
6-[3-(1,1-dimethyldecyl)-4-methoxyphenyl]-2-naphthoic acid.

In particular, preference will be given to adapalene and its salts.

The term "salts of adapalene" means the salts formed with a pharmaceutically acceptable base, in particular inorganic bases, such as sodium hydroxide, potassium hydroxide and ammonia, or organic bases, such as lysine, arginine or N-methylglucamine.

The term "salts of adapalene" also means the salts formed with fatty amines, such as dioctylamine and stearylamine.

Of course, the amount of the two active agents, benzoyl peroxide and retinoid, in the compositions according to the invention will depend on the combination selected and thus particularly on the retinoid under consideration and on the quality of the treatment desired.

The preferred retinoid concentrations are from 0.0001 to 20% by weight, with respect to the total weight of the composition.

Preferably, in the case of adapalene, the compositions according to the invention comprise from 0.001% to 5% by weight and advantageously from 0.01% to 1% by weight of adapalene, with respect to the total weight of the composition, preferentially from 0.01% to 0.5% by weight, preferably from 0.1% to 0.4% by weight of adapalene, more preferably still 0.3% by weight of adapalene.

The benzoyl peroxide can just as easily be employed in the free form or else in an encapsulated form, for example in a form adsorbed on or absorbed in any porous support. It can, for example, be benzoyl peroxide encapsulated in a polymeric system composed of porous microspheres, such as, for example, microsponges marketed under the trademark of Microsponges P009A Benzoyl Peroxide by Amcol.

To provide an order of magnitude, the compositions according to the invention advantageously comprise from 0.0001% to 20% by weight of benzoyl peroxide and from 0.0001% to 20% by weight of retinoid, with respect to the total weight of the composition, and preferably from 0.025% to 10% by weight of benzoyl peroxide and from 0.001% to 10% by weight of retinoid respectively, with respect to the total weight of the composition.

For example, in the compositions for the treatment of acne, the benzoyl peroxide is preferably included at concentrations ranging from 2% to 10% by weight and more particularly from 2.5% to 5% by weight, with respect to the total weight of the composition. The retinoid for its part is included in this type of composition at concentrations generally ranging from 0.01% to 1% by weight, with respect to the total weight of the composition.

Advantageously, the particle size of the retinoid and of the benzoyl peroxide is such that at least 80% by number of the particles and preferably at least 90% by number of the particles have a diameter of less than 25 µm and at least 99% by number of the particles have a diameter of less than 100 µm.

Preferably, the cream gel according to the invention comprises one or more gelling agents and/or suspending agents and/or pH-independent gelling agents.

The term "pH-independent gelling agent" means a gelling agent capable of conferring a viscosity on the composition sufficient to keep the retinoid and the benzoyl peroxide in suspension, even under the influence of a variation in pH due to the release of benzoic acid by the benzoyl peroxide.

Exemplary are, as non-limiting examples of gelling agents and/or suspending agents and/or pH-independent gelling agents which can participate in the compositions according to the invention, of the acrylates/$C_{10\text{-}30}$ alkyl acrylate crosspolymer marketed under the trademark of Pemulen TR-1 or Pemulen TR-2 by Noveon, "electrolyte-insensitive" carbomers, marketed under the trademark of Ultrez 20®, Carbopol 1382 or Carbopol ETD2020NF® by Noveon, polysaccharides, with, as non-limiting examples, xanthan gum, such as the Xantural 180®, marketed by Kelco, guar gum, chitosans, carrageenans, in particular divided into four main families: κ, λ, β and ω, such as the Viscarin® products and Gelcarin® products marketed by IMCD, cellulose and its derivatives, such as hydroxypropylmethylcellulose, in particular the product marketed under the trademark of Methocel E4 Premium by Dow Chemical, or hydroxyethylcellulose, in particular the product marketed under the trademark of Natrosol HHX 250° by Aqualon, or also the product "microcrystalline cellulose and carboxymethyl cellulose sodium" marketed under the trademark of Avicel CL-611 by FMC Biopolymer, the family of magnesium aluminum silicates, such as Veegum K, marketed by Vanderbilt, the family of acrylic polymers coupled to hydrophobic chains, such as the PEG-150/decyl/SMDI copolymer marketed under the trademark of Aculyn 44 (polycondensate comprising at least, as components, a polyethylene glycol comprising 150 or 180 mol of ethylene oxide, decyl alcohol and methylenebis(4-cyclohexyl isocyanate) (SMDI), at 35% by weight in a mixture of propylene glycol (39%) and water (26%)), the family of modified starches, such as the modified potato starch marketed under the trademark of Structure Solanace, and also their mixtures, and gelling agents of the family of polyacrylamides, such as the sodium acryloyldimethyltaurate copolymer/isohexadecane/polysorbate 80 mixture marketed under the trademark Simulgel 600PHA by Seppic or the polyacrylamide/C13-14 isoparaffin/laureth-7 mixture, such as, for example, that marketed under the trademark of Sepigel 305 by Seppic.

The preferred gelling agents result from the family of polyacrylamides, such as Simulgel 600PHA or Sepigel 305; "electrolyte-insensitive" carbomers, such as Carbopol ETD2020 NF; polysaccharides, such as xanthan gum; cellulose derivatives, such as hydroxypropylmethylcellulose or hydroxyethylcellulose; or magnesium aluminum silicates, alone or as a mixture.

The gelling agent or suspending agent as described above can be employed at the preferred concentrations ranging from 0.001% to 15% to more preferably ranging from 0.1% to 5%.

Exemplary are, among chelating agents, ethylenediaminetetraacetic acid (EDTA), diethylenetriaminepentaacetic acid (DTPA), ethylenediamindi(o-hydroxyphenylacetic acid) (EDDHA), (2-hydroxyethyl)ethylenediaminetriacetic acid (HEDTA), ethylenediamindi(o-hydroxy-p-methylphenylacetic acid) (EDDHMA) and ethylenediamindi(5-carboxy-2-hydroxyphenylacetic acid) (EDDCHA).

A preferred chelating agent is ethylenediaminetetraacetic acid (EDTA).

The concentrations of chelating agent can vary from 0% to 1.5% by weight, preferably from 0.05% to 0.5% by weight, with respect to the total weight of the composition.

The compositions of the invention can comprise one or more wetting agents at concentrations of 0% to 20% by weight, preferably of 0% to 10% by weight, with respect to the total weight of the composition. When these ingredients are present in the composition, they are at concentrations ranging from 0.001% to 20% by weight, preferentially from 0.1% to 10% by weight, preferably from 0.1% to 7% by weight and more preferably still from 2% to 7% by weight, with respect to the total weight of the composition. They should not dissolve the active principles at the percentage used, should not cause exothermic reactions harmful to the benzoyl peroxide, should help in dispersing the active principles well and should have anti-foaming properties. The wetting power is the tendency of a liquid to spread out over a surface.

Preferably, the wetting agents are ones which can exhibit an HLB (Hydrophilic-Lipophilic Balance) of 7 to 16. Exemplary are the Poloxamers and more particularly Synperonic PE/L44 and/or Synperonic PE/L62, marketed by Uniqema, glycols, such as propylene glycol, dipropylene glycol, propylene glycol dipelargonate, lauroglycol or ethoxydiglycol, sorbitan esters, such as POE (20) sorbitan monooleate, marketed under the trademark of Tween 80 by Uniqema, and POE (20) sorbitan monostearate, marketed under the trademark of "Tween 60" by Uniqema, ethers of fatty alcohols, such as Ceteareth-20, marketed under the trademark of Eumulgin B2 by Cognis, glycerol esters, such as glycerol monostearate, marketed under the trademark of "Cutina GMS" by Cognis, polyoxyethylene (21) stearyl ether, marketed under the trademark of Brij 721 by Uniqema, methyl glucose sesquistearate, marketed under the trademark of Glucate SS by Noveon, or PEG-20 methyl glucose sesquistearate, marketed under the trademark of Glucamate SSE-20 by Noveon.

Preferred wetting agents, which can preferably exhibit an HLB of 10 to 14, are compounds of the family of the Poloxamers and more particularly Synperonic PE/L44 and/or Synperonic PE/L62 or of glycols, such as propylene glycol, dipropylene glycol, propylene glycol dipelargonate, lauroglycol or ethoxydiglycol.

The particularly preferred wetting agents are propylene glycol or Synperonic PE/L44 (polyethylene-polypropylene glycol; polyoxyethylene-polyoxypropylene block copolymer).

According to the invention, the cream gel comprising the benzoyl peroxide and a retinoid advantageously comprises at least water and at least one gelling agent and/or suspending agent and/or pH-independent gelling agent and can also comprise one or more wetting agents.

The compositions according to the invention also comprise a fatty phase. This fatty phase can comprise lipophilic compounds, alone or as a mixture, such as, for example, vegetable, mineral, animal or synthetic oils, silicone oils and mixtures thereof.

Exemplary mineral oils are liquid paraffins with different viscosities, such as Primol 352®, Marcol 82® or Marcol 152°, marketed by Esso.

Exemplary vegetable oils are sweet almond oil, palm oil, soybean oil, sesame oil or sunflower oil.

Exemplary animal oils are lanolin, squalene, fish oil or mink oil, with, as derivative, the squalane marketed under the trademark Cosbiol® by Laserson.

Exemplary synthetic oils are an ester, such as cetearyl isononanoate, for example the product marketed under the trademark of Cetiol SN PH® by Cognis France, isopropyl palmitate, for example the product marketed under the trademark of Crodamol IPP® by Croda, diisopropyl adipate, marketed under the trademark of Crodamol DA by Croda, or caprylic/capric triglyceride, such as Miglyol 812®, marketed by Hüls/Univar.

Exemplary volatile or non-volatile silicone oils are dimethicones, such as the products marketed under the trademark of Q7-9120 Silicone Fluid with a viscosity of from 20 cSt and 12 500 cSt or the product marketed under the trademark ST-Cyclomethicone-5 NF® by Dow Corning.

Solid fatty substances can also be included, such as natural or synthetic waxes. In this case, one skilled in this art will adjust the heating temperature of the preparation according to the presence or absence of these solids.

For the compositions according to the invention, synthetic oils and silicone oils and more particularly Marcol 152® and ST-Cyclomethicone 5 NF® are preferred.

The aqueous phase of the cream gels according to the invention can comprise water. This water can in particular be a floral water, such as cornflower water, or a natural thermal or mineral water, for example selected from among water from Vittel, waters from the Vichy basin, water from Uriage, water from La Roche-Posay, water from Avène or water from Aix-les-Bains.

The said aqueous phase can be present at a content of from 10% to 90% by weight, with respect to the total weight of the composition, preferably from 20% to 80% by weight.

The compositions can additionally comprise any additive conventionally used in the cosmetics or pharmaceutical field, such as a stabilizing agent for benzoyl peroxide (by way of example, sodium docusate or sodium $C_{14-16}$ olefinsulphonate), neutralizing agents of normal inorganic or organic base or acid type (by way of example, triethanolamine, 10% sodium hydroxide solution, the citric acid/sodium citrate buffer or the succinic acid/sodium succinate buffer), antioxidants, sunscreens, preservatives, fillers, electrolytes, humectants and/or emollients, colorants, fragrances, essential oils, cosmetic active principles, moisturizing agents, vitamins, essential fatty acids, sphingolipids, self-tanning compounds, such as DHA, soothing agents and protective agents for the skin, such as allantoin. Of course, one skilled in this art will take care to select this or these optional additional compounds and/or their amounts in such a way that the advantageous properties of the compositions according to the invention are not, or not substantially, detrimentally affected.

These additives can be present in the composition in a proportion of 0.001% to 20% by weight, with respect to the total weight of the composition.

Exemplary preservatives are benzalkonium chloride, bronopol, chlorhexidine, chlorocresol and its derivatives, ethyl alcohol, phenethyl alcohol, phenoxyethanol, potassium sorbate, diazolidinylurea, benzyl alcohol, parabens or their mixtures.

Exemplary humectants and/or emollients are glycerol and sorbitol, sugars (by way of example, glucose or lactose), PEGs (by way of example, Lutrol E400), urea or amino acids (by way of example, serine, citrulline or alanine).

In particular, the present invention also features pharmaceutical or cosmetic compositions in the form of a cream gel comprising, formulated into a physiologically acceptable medium compatible with topical application to the skin, superficial body growths or mucous membranes, the ingredients (expressed as percentage by weight) selected from among:

from 0.001% to 5%, preferably from 0.01% to 0.5%, of a retinoid and preferably of a naphthoic acid derivative;

from 0.025% to 10%, preferably from 2% to 10%, of benzoyl peroxide;

from 30% to 95%, preferably from 50% to 85%, of water;

from 0.01% to 15%, preferably from 0.1% to 5%, of one or more gelling agents and/or suspending agents and/or pH-independent gelling agents;

from 2% to 50%, preferably from 5% to 30%, of fatty phase;

from 0% to 1.5%, preferably from 0.05% to 0.5%, of chelating agents;

from 0% to 10%, preferably from 2% to 7%, of one or more wetting agents;

from 0% to 3%, preferably from 0.05% to 1%, of preservatives;

from 0% to 20%, preferably from 2% to 15%, of humectants and/or emollients;

from 0% to 3%, preferably from 0.05% to 2%, of stabilizing agents;

from 0% to 10%, preferably from 0.1% to 5%, of neutralizing agents.

The present invention also features administration of the compositions as described above as medicaments.

The invention also features the use of the novel compositions as described above in cosmetics and in dermatology.

Due to the keratolytic, bactericidal and anti-inflammatory activity of benzoyl peroxide and the marked activity of retinoids in the fields of cell differentiation and proliferation, the compositions of the invention are particularly well suited for the following therapeutic fields:

1) for treating dermatological conditions linked to a disorder of keratinization involving differentiation and proliferation, in particular for treating acne vulgaris, comedonic or polymorphic acne, acne rosacea, nodulocystic acne, acne conglobata, senile acne, secondary acnes, such as solar, drug or occupational acne, or hidradenitis suppurativa, 2) for treating other types of disorders of keratinization, in particular ichthyoses, ichthyosiform conditions, Darier's disease, palmoplantar keratoderma, leucoplakia and leucoplakiform conditions, or cutaneous or mucosal (oral) lichen, 3) for treating other dermatological conditions linked to a disorder of keratinization with an inflammatory and/or immunoallergic component and, in particular, all forms of psoriasis, whether cutaneous, mucosal or ungual, and even psoriatic rheumatism, or alternatively cutaneous atopy, such as eczema, or respiratory atopy or alternatively gingival hypertrophy; the compounds can also be used in some inflammatory conditions not exhibiting disorder of keratinization, such as folliculitis, 4) for treating all dermal or epidermal proliferations, whether they are benign or malignant and whether they are or are not of viral origin, such as common warts, flat warts, molluscum contagiosum and epidermodysplasia verruciformis, florid or oral papillomatoses, and the proliferations which can be induced by ultraviolet radiation, in particular in the case of actinic keratoses, 5) for repairing or combating skin aging, whether photoinduced or chronologic, or for reducing pigmentations, or any pathology associated with chronologic or actinic aging;

6) for preventively or curatively treating disorders of cicatrization or skin ulcers, for preventing or repairing stretch marks, or alternatively for promoting cicatrization, 7) for combating disorders of the sebaceous function, such as hyperseborrhoea of acne or simple seborrhoea, 8) in the treatment of any condition of fungal origin on the skin, such as tinea pedis and tinea *versicolor*, 9) in the treatment of dermatological conditions with an immunological component, 10) in the treatment of skin disorders due to exposure to UV radiation, and 11) in the treatment of dermatological conditions linked to inflammation or infection of the tissues surrounding the hair follicle, in particular due to microbial colonization or infection, in particular impetigo, seborrhoeic dermatitis, folliculitis or sycosis barbae, or involving any other bacterial or fungal agent.

The compositions according to the invention are particularly useful for the preventive or curative treatment of acne vulgaris.

This invention also features pharmaceutical compositions intended for the prevention and/or treatment of dermatological conditions linked to disorders of cell differentiation and/or proliferation and/or of keratinization, preferably acne vulgaris.

The compositions according to the invention are also useful in body and hair hygiene.

The present invention thus also features the cosmetic administration of a composition according to the invention for the treatment of skin with a tendency towards acne, for causing hair growth or preventing hair loss, for combating the greasy appearance of the skin or hair, in protecting against the harmful effects of the sun or for preventing and/or combating photoinduced or chronologic aging.

Preferably, the said compositions according to the invention are administered topically.

The present invention also features a process for the preparation of a composition as described above. Such a process is characterized in that it comprises a stage of mixing a physiologically acceptable medium with at least one naphthoic acid derivative and at least benzoyl peroxide.

The other optional excipients and additives will be introduced according to the chemical nature of the compounds and the formulation form selected.

Generally, the preparation of a composition according to the invention is carried out according to the following main process:

a) mixing at least one retinoid with water until it has completely dispersed, to obtain active phase 1;

b) mixing the benzoyl peroxide with water until it has completely dispersed, to obtain active phase 2;

c) mixing at least one gelling agent and/or suspending agent and/or pH-independent gelling agent with water, optionally one or more chelating agents, one or more preservatives, one or more humectants and/or emollients, one or more stabilizing agents and the hydrophilic additives, to obtain the aqueous phase;

d) optionally, mixing at least two lipophilic compounds, to obtain the fatty phase;

e) mixing the 2 active phases obtained in a) and b), to obtain a single active phase;

f) introducing the single active phase obtained in e) into the aqueous phase obtained in c);

g) introducing the single compound of the fatty phase or optionally the fatty phase obtained in d), to obtain a cream gel;

h) if necessary, the heat-sensitive additives are added;

i) if necessary, a neutralizing agent for the gelling agent is introduced into the cream gel obtained in g) or h);

j) if necessary, further water is added.

Generally, the formulation of a composition according to the invention takes place thus according to the following alternative process:

a') Stages a) and b) are combined, so as to obtain stage a'), which corresponds to the mixing of at least one retinoid and benzoyl peroxide with water and at least one wetting agent until they have completely dispersed, to obtain the single active phase.

Stages c), d), f), g), h), i) and j) of the main process remain unchanged. As regards step e), this is deleted.

According to a specific embodiment, the preparation of a composition according to the invention takes place, by way of example, according to the following main process:

a) the retinoid, preferably the naphthoic acid derivative, is mixed with at least one wetting agent in water until the said naphthoic acid derivative has completely dispersed, to obtain active phase 1;

b) the benzoyl peroxide is mixed with at least one wetting agent in water until it has completely dispersed, to obtain active phase 2;

c) one or more gelling agents and/or suspending agents and/or pH-independent gelling agents (with the exception of the polyacrylamide) and optionally one or more chelating agents, one or more preservatives, one or more humectants and/or emollients, one or more stabilizing agents and the heat-insensitive hydrophilic additives are dissolved in the water with stirring, if necessary under hot conditions. Stirring is maintained and optional heating is maintained until homogeneity is achieved, to obtain the aqueous phase;

d) optionally, at least oils, and optionally solid fatty substances, and preservatives and the heat-insensitive lipophilic additives are mixed, if necessary under hot conditions, until homogeneity is achieved, to obtain the fatty phase;

e) active phases 1 and 2 are mixed, so as to obtain a single active phase;

f) the single active phase obtained in e) is added to the aqueous phase obtained in c);

g) optionally, the polyacrylamide is introduced into the phase obtained in f), h) the single fatty phase constituent or optionally the said fatty phase obtained in d) is introduced into the phase obtained in f) or g), to obtain a cream gel;

i) if necessary, the heat-sensitive additives are added;

j) if necessary, a neutralizing agent for the gelling agent is introduced into the cream gel obtained in h) or i), to obtain the desired pH;

k) if necessary, further water is added.

In particular, the formulation of a composition according to the invention takes place thus according to the following alternative process:

a') Stages a) and b) are combined, so as to obtain stage a'), which corresponds to the mixing of at least one retinoid and benzoyl peroxide with water and at least one wetting agent until they have completely dispersed, to obtain the single active phase.

Stages c), d), f), g), h), i), j) and k) of the main process remain unchanged. As regards stage e), it is deleted.

More specifically, by way of example, the main process for the preparation of the compositions according to the invention comprises the following stages:

Stage a: Preparation of Active Phase 1:

The active principle (adapalene), a portion of the purified water and the wetting agent or agents (propylene glycol, Synperonic PE/L62, Synperonic PE/L44 type) are weighed in a beaker. They are dispersed with stirring until they have completely dispersed.

Stage b: Preparation of Active Phase 2:

The active principle (benzoyl peroxide), a portion of the purified water and the wetting agent or agents (propylene glycol, Synperonic PE/L62, Synperonic PE/L44 type) are weighed in a beaker. They are dispersed with stirring until they have completely dispersed.

Stage c: Preparation of the Aqueous Phase:

The remaining purified water, the gelling agent or agents (Carbopol, Pemulen TR1, Xantural, Methocel type) and/or suspending agent or agents (Avicel CL-611 type) and/or pH-independent gelling agent or agents (with the exception of Simulgel 600PHA) and optionally one or more chelating agents (EDTA type), one or more humectants and/or emollients (glycerol type), one or more stabilizing agents (sodium docusate type), one or more preservatives (methylparaben type) and the heat-insensitive hydrophilic additives are introduced with stirring into a beaker, if necessary under hot conditions. Stirring is maintained and optional heating is maintained until the mixture is completely homogeneous.

Stage d: Preparation of the Fatty Phase (Optional):

The oily compounds (Olepal isostearique, Cetiol SN, Crodamol DA, Speziol C18, Miglyol 812, Cosbiol type), the optional heat-insensitive lipophilic additives, if heating, and optionally the preservatives (phenoxyethanol, propylparaben type) are mixed in a beaker. The mixture is heated until homogeneity is achieved and the volatile silicone, if the latter is present in the composition, is introduced.

Stage e: Mixing the Active Phases:

The two active phases respectively obtained in a) and b) are mixed at a temperature of less than 40° C. and stirring is maintained until the mixture is completely homogeneous.

Stage f: Introduction of the Single Active Phase into the aqueous phase:

The single active phase obtained in stage e) is introduced into the aqueous phase obtained in stage c).

Stage g: (Optional) Addition of the Simulgel 600PHA:

The Simulgel 600PHA is introduced with stirring into the phase obtained in f). Stirring is maintained until the Simulgel has completely dispersed.

Stage h: Addition of the Oil or of the Fatty Phase Obtained in d):

The single fatty phase constituent or optionally the fatty phase obtained in stage d) is introduced into the mixture obtained in f) or g).

Stage i (Optional): Addition of the Heat-Sensitive Additives:

The optional additives are introduced with stirring at a temperature below 40° C. Stirring is maintained until the mixture is completely homogeneous.

Stage j (Optional): Neutralization:

The neutralization agent for the gelling agent (such as triethanolamine, the 10% sodium hydroxide solution, the citric acid/sodium citrate buffer, the succinic acid/sodium succinate buffer) or the pH buffer is introduced, if necessary, at a temperature below 40° C. until at the desired pH. The product then assumes a thicker consistency. If necessary, the adjustment to 100% with water is carried out. The product is homogenized a final time to ensure the active principles, adapalene and benzoyl peroxide, are satisfactorily dispersed (microscopic observation revealing a homogeneous and aggregate-free dispersion) and then the product is packaged.

Stage k: Correction of the Water Loss:

The water loss during the preparation of the product is calculated and the lost water is re-added with stirring. Stirring is maintained until the mixture is completely homogeneous.

More specifically, by way of example, the alternative process for the preparation of the composition according to the invention comprises the following stages:

Stage a': Preparation of the Single Active Phase:

Stages a) and b) of the main process are combined, so as to obtain stage a'), which corresponds to the mixing of at least one retinoid and benzoyl peroxide with water and at least one wetting agent until they have completely dispersed, to obtain the single active phase.

Stages c), d), f), g), h), i), j) and k) of the main process remain unchanged. As regards stage e), this is deleted.

In order to further illustrate the present invention and the advantages thereof, the following specific examples are given, it being understood that same are intended only as illustrative and in nowise limitative. In said examples to follow, all parts and percentages are given by weight, unless otherwise indicated.

The formulation examples below illustrate the compositions according to the invention without, however, limiting the scope thereof.

The term "physical stability of the formulations" means carrying out macroscopic and microscopic observation at ambient temperature and 40° C., carried out at T1 month and T2 months.

Microscopic observation makes it possible to evaluate the quality of the dispersion of the two active principles. The adapalene is observed in fluorescent light while the benzoyl peroxide is observed in polarized light.

The characterization of the finished product is completed by a measurement of the yield point and of viscosity.

For the measurement of the yield point, use is made of a Haake rheometer of VT550 type with an SVDIN measuring spindle.

The rheograms are produced at 25° C. and at the shear rate of 4 $s^{-1}$, 20 $s^{-1}$ and 100 $s^{-1}$ ($\gamma$), the shear stress being measured. The term "yield point" ($\tau 0$, expressed in pascals) means the force necessary (minimum shear stress) to overcome the cohesive forces of Van der Waals type and to bring about flow. The yield point is to be equated with the value found at the shear rate of 4 $s^{-1}$.

For the viscosity measurement, use is made of Brookfield RVDVII+ or LDVDII+ viscometers. The viscosity ranges which can be measured with the two Brookfield types are as follows:

RVDVII+: 100 cP-40 McP

LVDVII+: 15 cP-6 McP

The chemical stability is ensured by an HPLC quantitative determination of the active principles.

The result is expressed in g/g of adapalene and of benzoyl peroxide and as % with respect to the expected content.

Example 1: Formulation of Cream Gel Type Comprising 0.1% Adapalene and 2.5% Benzoyl Peroxide The formulation is prepared according to the procedure described above.

| Constituents | Content (% w/w) |
| --- | --- |
| Benzoyl peroxide | 2.50 |
| Adapalene | 0.10 |
| Propylene glycol | 5.00 |
| Synperonic PE/L44 | 0.20 |
| EDTA | 0.10 |
| Glycerol | 5.00 |
| Xantural 180 | 0.10 |
| Carbopol Ultrez 20 | 0.70 |
| Marcol 152 | 7.00 |
| Purified water | q.s. for 100% |
| Sodium hydroxide, 10% w/w | q.s. for pH 5.5 ± 0.5 |

Stability Data:
Physical Stability:

| Characterizations at T0 | |
| --- | --- |
| Macroscopic appearance | White cream gel |
| Microscopic appearance | Dispersion of the active principles without aggregates of greater than 100 μm |
| pH | 5.144 |
| Viscosity data Haake (4 $s^{-1}$/20 $s^{-1}$/100 $s^{-1}$) | 94/123/187 |
| Brookfield RVDVII+ (S28; 5 rpm) | 65 620 cP |

-continued

|  |  | T + 1 month | T + 2 months | T + 3 months |
|---|---|---|---|---|
| Macroscopic appearance | AT | Identical to T0 | Identical to T0 | Identical to T0 |
|  | 40° C. | Identical to T0 | Identical to T0 | Identical to T0 |
| Microscopic appearance | AT | Identical to T0 | Identical to T0 | Identical to T0 |
|  | 40° C. | Identical to T0 | Identical to T0 | Identical to T0 |
| pH | AT | 5.10 | 5.03 | 5.09 |
|  | 40° C. | 4.96 | 4.74 | 4.59 |
| Haake rheology 4 s$^{-1}$/20 s$^{-1}$/100 s$^{-1}$ |  | 89/121/172 | 87/117/168 | N.R. |
| Brookfield RVDVII+ viscosity (S28; 5 rpm) |  | 65 775 cP | 63 820 cP | 67 505 cP |

Chemical Stability:

Adapalene:

|  |  | | Time | |
|---|---|---|---|---|
| Stability conditions |  | T0 | T + 1 month | T + 2 months |
| AT | g/g | 0.10 | 0.10 | 0.10 |
|  | % of the expected content | 100 | 100 | 100 |
| 40° C. | g/g | N.A. | 0.10 | 0.11 |
|  | % of the expected content | N.A. | 100 | 110 |

Benzoyl Peroxide:

|  |  | | Time | |
|---|---|---|---|---|
| Stability conditions |  | T0 | T + 1 month | T + 2 months |
| AT | g/g | 2.7 | 2.7 | 2.7 |
|  | % of the expected content | 108 | 108 | 108 |
| 40° C. | g/g | N.A. | 2.6 | 2.6 |
|  | % of the expected content | N.A. | 104 | 104 |

Example 2: Formulation of Thick Cream Gel Type Comprising 0.1% Adapalene and 2.5% Benzoyl Peroxide The formulation is prepared according to the procedure described above.

| Constituents | Content (% w/w) |
|---|---|
| Benzoyl peroxide | 2.50 |
| Adapalene | 0.10 |
| Propylene glycol | 6.00 |
| Synperonic PE/L44 | 0.20 |
| Glycerol | 5.00 |
| ST-Cyclomethicone 5NF | 7.00 |
| Simulgel 600 PHA | 4.00 |
| Purified water | q.s. for 100% |

Physical Stability:

| Characterizations at T0 | |
|---|---|
| Macroscopic appearance | White cream gel |
| Microscopic appearance | Dispersion of the active principles without aggregates of greater than 100 μm |
| pH | 3.542 |
| Viscosity data — Haake (4 s$^{-1}$/20 s$^{-1}$/100 s$^{-1}$) | 236/296/449 |
| Brookfield RVDVII+ (S29; 5 rpm) | 164 650 cP |

|  |  | T + 1 month | T + 2 months | T + 3 months |
|---|---|---|---|---|
| Macroscopic appearance | AT | Identical to T0 | Identical to T0 | Identical to T0 |
|  | 40° C. | Identical to T0 | Identical to T0 | Identical to T0 |
| Microscopic appearance | AT | Identical to T0 | Identical to T0 | Identical to T0 |
|  | 40° C. | Identical to T0 | Identical to T0 | Identical to T0 |
| pH | AT | 3.47 | 3.36 | 3.50 |
|  | 40° C. | 3.31 | 3.17 | 3.27 |
| Haake rheology 4 s$^{-1}$/20 s$^{-1}$/100 s$^{-1}$ |  | 223/286/389 | 201/268/334 | N.R. |
| Brookfield RVDVII+ viscosity (S29; 5 rpm) |  | 159 070 cP | 150 160 cP | 132 720 cP |

Chemical Stability:

Adapalene:

|  |  | | Time | |
|---|---|---|---|---|
| Stability conditions |  | T0 | T + 1 month | T + 2 months |
| AT | g/g | 0.10 | 0.11 | 0.10 |
|  | % of the expected content | 100 | 110 | 100 |
| 40° C. | g/g | N.A. | 0.10 | 0.10 |
|  | % of the expected content | N.A. | 100 | 100 |

Benzoyl Peroxide:

|  |  | | Time | |
|---|---|---|---|---|
| Stability conditions |  | T0 | T + 1 month | T + 2 months |
| AT | g/g | 2.7 | 2.8 | 2.7 |
|  | % of the expected content | 108 | 112 | 108 |
| 40° C. | g/g | N.A. | 2.6 | 2.6 |
|  | % of the expected content | N.A. | 104 | 104 |

Example 3: Formulation of Fluid Cream Gel Type Comprising 0.3% Adapalene and 1% Benzoyl Peroxide The formulation is prepared according to the procedure described above.

| Constituents | Content (% w/w) |
|---|---|
| Benzoyl peroxide | 1.00 |
| Adapalene | 0.30 |
| Lauroglycol | 2.00 |
| Synperonic PE/L62 | 0.20 |

-continued

| Constituents | Content (% w/w) |
| --- | --- |
| EDTA | 0.10 |
| Methylparaben | 0.20 |
| Methocel E4M Premium | 0.10 |
| Carbopol ETD202NF | 0.30 |
| Olepal isostearique | 2.00 |
| Cosbiol | 8.00 |
| Cetiol SN PH | 8.00 |
| Propylparaben | 0.05 |
| Sodium hydroxide, 10% w/w | q.s. for pH 5.5 ± 0.5 |
| Purified water | q.s. for 100% |

Example 4: Formulation of Fluid Cream Gel Type Comprising 0.10% Adapalene and 0.25% Benzoyl Peroxide The formulation is prepared according to the procedure described above.

| Constituents | Content (% w/w) |
| --- | --- |
| Benzoyl peroxide | 0.25 |
| Adapalene | 0.10 |
| Propylene glycol | 2.00 |
| Synperonic PE/L62 | 0.20 |
| EDTA | 0.10 |
| Glycerol | 5.00 |
| Methylparaben | 0.20 |
| Carbopol Ultrez-20 | 0.30 |
| Veegum K | 0.20 |
| Xanthan gum | 0.20 |
| ST-Cyclomethicone 5NF | 7.00 |
| Propylparaben | 0.10 |
| Triethanolamine | q.s. for pH 5.5 ± 0.5 |
| Purified water | q.s. for 100% |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for the treatment of acne, comprising topically applying to the skin of an individual in need thereof, an effective amount of a stable cream gel dermatological composition comprising, in a single formulation,
    (a) a homogeneous dispersion of a fatty phase in an aqueous phase, comprising at least one dispersed retinoid and dispersed benzoyl peroxide as a single active phase;
    (b) at least one lipophilic compound, other than the retinoid, selected from the group consisting of liquid paraffins, sweet almond oil, palm oil, soybean oil, sesame oil, sunflower oil, lanolin, squalene, fish oil, mink oil, squalane, cetearyl isononanoate, diisopropyl adipate, caprylic/capric triglyceride, a volatile or non-volatile silicone oil and natural or synthetic waxes; and
    (c) at least one gelling agent;
    formulated into a physiologically acceptable medium,
    wherein the fatty phase comprises the at least one lipophilic compound in an amount from 5% to 30% by weight, relative to the total weight of the composition, and
    wherein the composition is devoid of any emulsifier.

2. The method of claim 1, wherein the composition comprises from 0.0001% to 20% by weight of the at least one retinoid, relative to the total weight of the composition.

3. The method of claim 1, wherein the composition comprises from 0.0001% to 20% by weight of benzoyl peroxide, relative to the total weight of the composition.

4. The method of claim 1, wherein the at least one retinoid comprises adapalene.

5. The method of claim 1, wherein the composition comprises from 0.001% to 15% by weight of the at least one gelling agent, relative to the total weight of the composition.

6. The method of claim 1, wherein the composition is solid.

7. The method of claim 1, wherein the acne is comedonic acne, polymorphic acne, acne rosacea, nodulocystic acne, acne conglobata, senile acne, solar acne, drug acne, or occupational acne.

8. The method of claim 1, wherein the acne is characterized by hyperseborrhea.

* * * * *